(12) United States Patent
Sato et al.

(10) Patent No.: US 6,380,448 B1
(45) Date of Patent: Apr. 30, 2002

(54) METHOD FOR RECOVERING STYRENE MONOMER FROM POLYSTYRENE RESIN BY USING A CATALYST

(75) Inventors: Takumi Sato; Mitsuo Masunari, both of Hiroshima (JP)

(73) Assignee: San Kaihatsu Kabushiki Kaisha, Hiroshima (JP)

( * ) Notice: Subject to any disclaimer, the term of this patent is extended or adjusted under 35 U.S.C. 154(b) by 0 days.

(21) Appl. No.: 09/591,103

(22) Filed: Jun. 8, 2000

(30) Foreign Application Priority Data

Jan. 3, 2000 (JP) .......................................... 12-055832
Apr. 6, 2000 (JP) .......................................... 12-105518

(51) Int. Cl.⁷ .......................... C07C 4/24; B01J 27/053; B01J 27/055
(52) U.S. Cl. ........................ 585/439; 585/241; 502/217; 502/218
(58) Field of Search ................................ 585/439, 241; 502/217, 218

(56) References Cited

FOREIGN PATENT DOCUMENTS

GB        757752        *   9/1956

* cited by examiner

Primary Examiner—Thuan D. Dang
(74) Attorney, Agent, or Firm—Cislo & Thomas LLP

(57) ABSTRACT

The present invention relates to a method for recovering styrene monomers from polystyrene resins by using sulfate as a catalyst. The present invention makes possible to thermally decompose polystyrene resins at comparatively low temperatures, and to reduce facility costs, etc., and also makes possible to recover oil containing less ratio of low molecular weight components and a high content of styrene monomers from vapors obtained through thermal decomposition of polystyrene.

4 Claims, 23 Drawing Sheets

FIG. 4

| | CHROMATOPAC | C-R6A | | | FILE | 5 |
|---|---|---|---|---|---|---|
| | SAMPLE NO. | 0 | | | METHOD | 0041 |
| | REPORT NO. | 1826 | | | | |

| PKNO | TIME | AREA | MK | IDNO | CONC | NAME |
|---|---|---|---|---|---|---|
| 1 | 3.982 | 1889 | V | | 0.0891 | |
| 2 | 4.983 | 2136 | V | | 0.1052 | |
| 3 | 5.383 | 970 | | | 0.0477 | |
| 4 | 6.467 | 51573 | | | 2.5394 | toluene |
| 5 | 8.365 | 2827 | | | 0.1392 | |
| 6 | 9.142 | 17824 | | | 0.8776 | ethylbenzene |
| 7 | 10.328 | 1828173 | | | 90.0156 | styrene monomer |
| 8 | 11.217 | 1260 | | | 0.8620 | |
| 9 | 11.683 | 3706 | | | 0.1825 | |
| 10 | 11.930 | 581 | V | | 0.0286 | |
| 11 | 12.338 | 2654 | | | 0.1307 | |
| 12 | 12.512 | 35803 | V | | 1.7629 | |
| 13 | 13.477 | 2015 | | | 0.8992 | |
| 14 | 13.848 | 607 | V | | 0.0299 | |
| 15 | 14.017 | 699 | V | | 0.0344 | |
| 16 | 15.715 | 662 | | | 0.0326 | |
| 17 | 18.433 | 1108 | | | 0.0546 | |
| 18 | 18.847 | 792 | V | | 0.0390 | |
| 19 | 19.563 | 1001 | | | 0.0493 | |
| 20 | 20.442 | 10424 | | | 0.5133 | |
| 21 | 20.837 | 26367 | V | | 1.2982 | |
| 22 | 21.258 | 8385 | V | | 0.4129 | |
| 23 | 22.630 | 1433 | | | 0.0706 | |
| 24 | 25.977 | 1676 | | | 0.0025 | |
| 25 | 26.312 | 587 | V | | 0.0289 | |
| 26 | 26.973 | 18016 | V | | 0.8871 | |
| 27 | 28.308 | 4350 | | | 0.2142 | |
| 28 | 28.750 | 2087 | V | | 0.1028 | |
| 29 | 30.792 | 1428 | | | 0.0703 | |
| | TOTAL: | 2030950 | | | 100 | |

FIG. 7

```
C-R8A CHROMATOPAC CH=1   Report No.=7      DATA=1:@CHRM1.C00   00/04/06  15:48:50

** CALCULATION REPORT **
CH PKNO    TIME      AREA     HEIGHT   MK  IDNO    CONC       NAME
1    2     5.41     103592     36909                1.9955    toluene
     8     7.735     12265      2794                0.2363    ethylbenzene
    10     8.934   4991924    492831   S           96.1607    styrene monomer
    14    10.819      6548      2139                0.1261
    19    11.645     71320     31648                1.3738
    26    12.495      5585      2031   V            0.1076
                   ---------  --------             --------
           TOTAL   5191233    568351                 100
```

FIG. 9

```
C-R8A CHROMATOPAC CH=1   Report No.=3      DATA=1:@CHRM1.C00   00/03/25  11:13:38

** CALCULATION REPORT **
CH PKNO    TIME       AREA     HEIGHT    MK  IDNO.    CONC        NAME
1    1    5.502     130845     46620                  2.4536      toluene
     5    7.89       18902      4289                  0.3544      ethylbenzene
     6    9.131    5039946    489411                 94.5081      styrene monomer
     8   10.926      12350      4098                  0.2316
    13   11.743     125312     53439                  2.3498
    18   12.584       5467      2064    V             0.1025
                 ----------  --------              --------
         TOTAL     5332821    599920                100
```

FIG. 11

```
C-R8A CHROMATOPAC CH=1  Report No.=7      DATA=1:@CHRM1.C00   00/03/26  14:14:46

** CALCULATION REPORT **
CH PKNO   TIME     AREA     HEIGHT    MK  IDNO   CONC       NAME
1   1    5.455   127394     40970                2.2737     toluene
    7    7.86     30253      6303                0.5399
    8    8.192   302812     64261    V           5.4044     ethylbenzene
    9    9.1    5012567    477381                89.4618    styrene monomer
   12   10.932    5449       1800                0.0972
   14   11.516    6866       2698                0.1225
   15   11.744   111537     44987                1.9907
   18   12.591    6149       2411                0.1097
                ────────   ────────            ────────
        TOTAL   5603028    640810                 100
```

FIG. 13

```
C-R8A CHROMATOPAC CH=1   Report No.=1        DATA=1:@CHRM1.C00    00/03/25  09:17:22

** CALCULATION REPORT **
CH PKNO   TIME      AREA      HEIGHT    MK  IDNO   CONC          NAME
 1   1    5.587    117340      39009                 2.5875      toluene
     6    8.002     32376       7078                 0.7139      ethylbenzene
     7    9.219   4215459     430783                92.9584      styrene monomer
     9   11.005      5261       1823                 0.116
    12   11.797    149353      61790                 3.2935
    15   12.634      7195       2697    V            0.1587
    19   31.522      7796        914                 0.1719
                  --------   --------              --------
         TOTAL    4534778     544092                100
```

FIG. 15

```
C-R8A CHROMATOPAC CH=1  Report No.=3      DATA=1:@CHRM1.C00   00/03/30  11:16:18

** CALCULATION REPORT **
CH  PKNO   TIME      AREA      HEIGHT    MK   IDNO    CONC         NAME
1    1    5.417      54666      19302                 1.8501       toluene
     5    7.746      11025       2635                 0.3731       ethylbenzene
     7    8.877    2856751     352834                96.6863       styrene monomer
     9   10.823       7895       2616                 0.2672
    13   11.651      24323      10874                 0.8232
                   ─────────  ─────────             ─────────
         TOTAL    2954659     388261                  100
```

FIG. 17

```
C-R8A CHROMATOPAC CH=1  Report No.=4      DATA=1:@CHRM1.C00   00/03/30  12:00:54
** CALCULATION REPORT **
CH PKNO    TIME      AREA     HEIGHT    MK  IDNO    CONC        NAME
1    1    5.423     98774     35854                 3.3474      toluene
     6    7.757     26383      6360                 0.8941      ethylbenzene
     7    8.884   2717885    345668                92.1085      styrene monomer
    13   11.663    107700     48953                 3.6499
                  --------   -------                --------
         TOTAL    2950741    436836                  100
```

FIG. 19

```
C-RSA CHROMATOPAC CH=1  Report No.=2      DATA=1:@CHRM1.C00  00/03/31  10:12:22

** CALCULATION REPORT **
CH PKNO    TIME       AREA      HEIGHT    MK  IDNO    CONC         NAME
1   1     5.459       54898      18199                2.0112       toluene
    3     7.802       25607       5897                0.9381       ethylbenzene
    4     8.925     2593340     331988               95.0094       styrene monomer
    9    11.685       55716      23904                2.0412

TOTAL     2729560     379989                 100
```

FIG. 21

```
C-R8A CHROMATOPAC CH=1  Report No.=6      DATA=1:@CHRM1.C00   00/03/31  13:26:36
** CALCULATION REPORT **
CH PKNO    TIME       AREA     HEIGHT   MK  IDNO    CONC       NAME
 1   1    5.441      89999      32913             2.7867      toluene
     7    7.781      13367       3323             0.4139      ethylbenzene
     8    8.927    3047886     367496            94.3744      styrene monomer
    13   11.675      78318      33590             2.425
                  ---------   --------         --------
          TOTAL    3229570     437321              100
```

FIG. 23

```
C-R&A CHROMATOPAC CH=1   Report No.=15      DATA=1:@CHRM1.C00   00/03/31  20:50:36
** CALCULATION REPORT **
CH PKNO    TIME       AREA      HEIGHT    MK  IDNO    CONC          NAME
1    1    5.437      72912      26029                 2.5724        toluene
     5    7.773      38118       9020                 1.3448        ethylbenzene
     7    8.89     2563998     325561                90.4612        styrene monomer
     8   10.327      7046        2117                 0.2486
     9   10.839     42679       15599    S            1.5058
    13   11.67     109610       47775                 3.8672
                  ─────────   ─────────             ─────────
         TOTAL    2834361      426100                  100
```

FIG. 24

```
CHROMATOPAC    C-R6A                    FILE        5
SAMPLE NO    0                          METHOD      0041
REPORT NO    2014

PKNO      TIME      AREA      MK   IDNO    CONC      NAME 1      5.223     55434                  2.1073    toluene
   2      7.367      6085                  0.2313    ethylbenzene
   3      8.478   2389836                 90.851     styrene monomer
   4     10.517      3042                  0.1157
   5     11.432     50305    V             1.9124
   6     11.667       542    V             0.0206
   7     12.385      2432    V             0.0925
   8     12.747       925    V             0.0352
   9     13.013       591    V             0.0225
  10     14.473       972                  0.037
  11     17.233       999    V             0.038
  12     17.678     10318    V             0.3923
  13     17.848      2137    V             0.0812
  14     18.155       509    V             0.0193
  15     18.413       505    V             0.0192
  16     18.753     18219    V             0.6926
  17     19.162     75055    V             2.8533
  18     19.553      1696    V             0.0645
  19     19.725      1925    V             0.0732
  20     20.363       597    V             0.0227
  21     20.765      1427    V             0.0543
  22     24.353      6953                  0.2643
                  ---------             ------------
         TOTAL    2630502                 100
```

METHOD FOR RECOVERING STYRENE MONOMER FROM POLYSTYRENE RESIN BY USING A CATALYST

BACKGROUND OF THE INVENTION

1. Technical Field of the Invention

The present invention relates to a method for recovering styrene monomers from a polystyrene resin by using a catalyst, and its objective is to provide a method for recovering styrene monomers from polystyrene resin wastes at comparatively low temperatures with high yield.

2. Prior Art

Polystyrene resins are one type of industrial plastics which were developed earliest among thermoplastic resins, and since they are superior in moldability and inexpensive, they have been used in a wide range of applications.

Among these, foamed polystyrenes, which have been widely used as packaging materials for electric appliances, AV apparatuses, etc., cushioning materials for fix boxes, glass products, etc. and trays and heat insulating and cold reserving containers for food, etc., are bulky and are not decomposed even if they are buried in the soil; therefore, it is difficult to prepare a site for disposal. Moreover, since they have high burning temperatures, they tend to damage incinerators, and since they produce dioxin when mixed with a chlorine-containing material, it is difficult to dispose them through incineration; thus, they have raised major problems in industrial waste disposal.

Under such circumstances, a number of arts for recovering aromatic hydrocarbon oils such as styrene monomers from polystyrene resins have been proposed, and examples of them include those arts disclosed in JP No. 283745/1996 (Tokukaihei 8-283745), JP No. 221681/1997 (Tokukaihei 9-221681) and JP No. 302356/1997 (Tokukaihei 9-302356).

Any of these arts thermally decompose polystyrene resins under the presence of a catalyst; however, since the thermal decomposing process is carried out by heating polystyrene resins to high temperatures of 350 to 430° C., special plant facilities resistant to high temperatures are required, and such investments for facilities have increased initial costs.

Moreover, since recovered oils contain many components other than styrene monomers, the yield of styrene monomers becomes very low; for example, in the case of the method of JP No. 283745/1996, the ratio of styrene monomers contained in the recovered oils is as low as approximately 68 to 69%.

Here, JP No. 2545768 has disclosed a method for recovering styrene monomers from polystyrene resins by applying a heating process in a comparatively low temperature range of 300 to 350° C.; however, even by the application of this method, the content of the styrene monomers contained in the recovered oils is in the range of 60 to 79%, which fails to achieve a satisfactory level.

BRIEF SUMMARY OF THE INVENTION

The present invention has been devised to solve the above-mentioned problems, and its objective is to provide a method for recovering styrene monomers from polystyrene resins by using a catalyst, which can thermally decompose polystyrene resins at a comparatively low temperature so that it is possible to reduce the facility costs, etc., and which can recover oils that have less ratio of low molecular weight components and a high content of styrene monomers from the thermally decomposed vapor.

The present invention has been devised to solve the above-mentioned problems, and the invention according to claim 1 relates to a method for recovering styrene monomers from a polystyrene resin by using a catalyst, which obtains the styrene monomers by thermally decomposing the polystyrene resin, and which is characterized in that a sulfate is used as the catalyst.

The invention according to claim 2, which relates to the method of claim 1 for recovering styrene monomers from a polystyrene resin by using a catalyst, wherein the sulfate is a metal sulfate.

The invention according to claim 3, which relates to the method of claim 1 for recovering styrene monomers from a polystyrene resin by using a catalyst, wherein the sulfate is at least one member selected from the group consisting of magnesium sulfate, sodium sulfate, iron sulfate, manganese sulfate, zinc sulfate, aluminum sulfate, calcium sulfate, potassium sulfate and antimony sulfate.

The invention according to claim 4, which uses the method of claim 1 for recovering styrene monomers from a polystyrene resin by using a catalyst, wherein the heating temperature of the polystyrene resin is set to not more than 350° C.

PREFERRED EMBODIMENTS OF THE INVENTION

Referring to FIGS., the following description will discuss preferred embodiments of a method for recovering styrene monomers from polystyrene resin by using a catalyst in accordance with the present invention.

FIG. 1 is a schematic view that shows one example of a thermal decomposing device used in the present invention.

The thermal decomposing device (1) is constituted by a decomposing vessel (2) which houses material polystyrene resins (for example, polystyrene resin lumps having a fixed shape formed by air-releasing and pulverizing foaming polystyrene resins) inside thereof and thermally decomposes them, a supply section (3) for supplying the polystyrene resins to the decomposing vessel (2), a vapor outlet section (4) which externally releases thermally decomposed vapors generated in the decomposing vessel (2), a stirring device (5) for stirring and mixing the contents loaded inside the decomposing vessel (2), and a heating means, not shown.

Here, the device shown in FIG. 1 only schematically shows one example of the device used in the method of the present invention, and the device used in the method of the present invention is not intended to be limited thereby.

Polystyrene resins having a fixed shape formed by air-releasing and pulverizing, for example, foaming polystyrene are continuously supplied from the supply section (3) to the decomposing vessel (2), and to this decomposing vessel (2) is added a catalyst for accelerating thermal decomposition of the polystyrene resins.

The present invention is characterized by using a sulfate as this catalyst. Specifically, examples thereof include: zinc sulfate, aluminum sulfate, antimony sulfate, antimony (III) sulfate, ammonium sulfate, ammonium aluminum sulfate, ammonium chromium (III) sulfate, ammonium cobalt (II) sulfate, ammonium iron (II) sulfate, ammonium iron (III) sulfate, ammonium manganese (II) sulfate, iridium (III) sulfate, lead sulfate, lead sulfate ore, cadmium sulfate, potassium sulfate, gallium (III) sulfate, potassium aluminum sulfate, potassium chromium (III) sulfate, calcium sulfate, normal silver sulfate, guanidinium aluminum sulfate, chromium (II) sulfate, chromium (III) sulfate, cobalt (II) sulfate, cobalt (III) sulfate, zirconium (IV) sulfate, mercury (I) sulfate, hydrogen 3-indryl sulfate, hydrogen potassium sulfate, tin (II) sulfate, strontium sulfate, cerium (III) sulfate, cerium (IV) sulfate, titanium (III) sulfate, titanium (IV) sulfate, iron (II) sulfate, iron (III) sulfate, copper (II) sulfate, dodecyl sodium sulfate, thorium (IV) sulfate, sodium sulfate, sodium aluminum sulfate, lead (II) sulfate, lead (IV) sulfate, nickel (II) sulfate, nickel (II) aluminum sulfate, nitrosyl sulfate, disodium magnesium sulfate, neodymium (III) sulfate, vanadium (III) sulfate, barium sulfate, hydroxyl ammonium sulfate, praseodymium (III) sulfate, magnesium sulfate, magnesium dipotassium sulfate, manganese (II) sulfate, manganese (III) sulfate, lanthanum (III) sulfate, lignin sulfate, lithium sulfate, rubidium sulfate, rubidium aluminum sulfate, manganese (III) cesium sulfate.

Moreover, the following hydrates of these sulfates may be used: zinc sulfate monohydrate, zinc sulfate hexahydrate, zinc sulfate heptahydrate, aluminum sulfate hexahydrate, aluminum sulfate decahydrate, aluminum sulfate 16-hydrate, aluminum sulfate 18-hydrate, aluminum sulfate 27-hydrate, ammonium chromium (III) sulfate 12-hydrate, ammonium cobalt (II) sulfate hexahydrate, ammonium iron (II) sulfate hexahydrate, ammonium iron (III) sulfate 12-hydrate, ammonium manganese (II) sulfate hexahydrate, cadmium sulfate monohydrate, cadmium sulfate 8/3-hydrate, cadmium sulfate heptahydrate, cadmium aluminum 24-hydrate, potassium aluminum sulfate 12-hydrate, potassium aluminum sulfate 16-hydrate, potassium chromium (III) sulfate 12-hydrate, potassium chromium (III) sulfate hexahydrate, potassium chromium (III) sulfate trihydrate, potassium chromium (III) sulfate monohydrate, calcium sulfate dihydrate, chromium (II) sulfate heptahydrate, chromium (III) sulfate 18-hydrate, chromium (III) sulfate trihydrate, cobalt (II) sulfate hexahydrate, cobalt (II) sulfate monolydrate, cobalt (III) sulfate 18-hydrate, zirconium (IV) sulfate monohydrate, zirconium (IV) tetrahydrate, cerium (III) sulfate octahydrate, cerium (IV) sulfate tetrahydrate, titanium (IV) sulfate tetrahydrate, iron (III) sulfate monohydrate, iron (II) sulfate tetrahydrate, iron (II) sulfate pentahydrate, iron (II) sulfate heptahydrate, iron (III) sulfate trihydrate, iron (III) sulfate hexahydrate, iron (III) sulfate heptahydrate, iron (III) sulfate 7.5-hydrate, iron (III) sulfate nonahydrate, iron (III) sulfate decahydrate, iron (III) sulfate 12-hydrate, copper (II) sulfate pentahydrate, thorium (IV) sulfate dihydrate, thorium (IV) sulfate tetrahydrate, thorium (IV) sulfate hexahydrate, thorium (IV) sulfate octahydrate, thorium (IV) sulfate nonahydrate, sodium sulfate heptahydrate, sodium sulfate decahydrate, sodium aluminum sulfate 24-hydrate, nickel (II) sulfate monohydrate, nickel (II) sulfate dihydrate, nickel (II) sulfate tetrahydrate, nickel (II) sulfate heptahydrate, disodium magnesium sulfate 2.5-hydrate, disodium magnesium tetrahydrate, vanadium (II) sulfate heptahydrate, vanadium (III) sulfate trihydrate, vanadium (III) sulfate nonahydrate, magnesium sulfate monohydrate, magnesium sulfate 1.5-hydrate, magnesium sulfate dihydrate, magnesium sulfate trihydrate, magnesium sulfate hexahydrate, magnesium sulfate heptahydrate, magnesium dipotassium sulfate tetrahydrate, magnesium dipotassium sulfate hexahydrate, manganese (II) sulfate monohydrate, manganese (II) sulfate dihydrate, manganese (II) sulfate tetrahydrate, manganese (II) sulfate pentahydrate, manganese (II) sulfate heptahydrate, and manganese (III) cesium sulfate 12-hydrate.

Among the above-mentioned sulfates, metal sulfates are preferably used, and among the metal sulfates, magnesium sulfates, sodium sulfates, iron sulfates, manganese sulfates, zinc sulfates, aluminum sulfates, calcium sulfates, potassium sulfates, antimony sulfates, and hydrates of these sulfates are more preferably used.

One kind of these catalysts may be used, or two or more kinds of these may be used in combination.

Moreover, the above-mentioned catalyst, as it is, may be added, or the above-mentioned catalyst supported on a carrier may be added. With respect to the carrier, although not particularly limited, those superior in heat resistance, such as glass fiber, silica, alumina and titanium oxide, are preferably used.

With respect to the method for allowing the carrier to support the catalyst, it is not particularly limited; and a known method such as a dipping method and a co-precipitation method may be used.

Moreover, with respect to the shape of the catalyst, the catalyst may have a lump shape, a powder form or another shape; and those having a particle size of approximately 0.3 to 3.0 mm are preferably used.

In the present invention, the amount of the catalyst to be added is set in the range of 10 to 25 weight %, and more preferably, 10 to 20 weight %

The amount of addition of the catalyst less than 10 weight % fails to sufficiently exert the functions and effects of the application of the catalyst, and the amount thereof exceeding 25 weight % also fails to exert the corresponding effects, giving adverse effects on production costs.

Next, the following description will discuss one example of a method for recovering styrene monomers from polystyrene resins by using a catalyst in accordance with the present invention.

First, a polystyrene resin as a material (for example, air-released foaming polystyrene resin) is loaded inside the decomposing vessel (2) in the thermal decomposing device (1), and the above-mentioned catalyst is added to the inside of the decomposing vessel (2).

Next, this is heated while being mixed and stirred by the stirring device (5) so that the polystyrene resin is allowed to contact the catalyst so as to be thermally decomposed.

The heating temperature of the polystyrene resin, which is determined depending on the kinds of a catalyst to be used, is preferably set in the range of 230 to 350° C., more preferably, 250 to 330° C.

More specifically, for example, the preferable heating temperature ranges for the respective catalysts are shown as follows: in the case of magnesium sulfate, the temperature range is 230 to 330° C., in the case of iron sulfate, the temperature range is 200 to 310° C., in the case of sodium sulfate, the temperature range is 250 to 330° C. In the case of manganese sulfate, the temperature range is 200 to 350° C., in the case of zinc sulfate, the temperature range is 200 to 350° C., in the case of aluminum sulfate, the temperature range is 210 to 310° C., in the case of calcium sulfate, the temperature range is 220 to 310° C., in the case of potassium sulfate, the temperature range is 300 to 350° C., and in the case of antimony sulfate, the temperature range is 250 to 310° C.

Thermally decomposed vapors generated by the application of heat are taken out of the thermal decomposing device (1) through the vapor outlet section (4).

Then, the thermally decomposed vapors, taken out of the device is condensed and liquefied to obtain crude styrene monomer, and this crude styrene monomer is vacuum-distilled to recover a styrene monomer with high purity.

EXAMPLES

The following description will discuss the method for recovering styrene monomers from polystyrene resins by using a catalyst of the present invention by means of examples so as to clarify the effects of the present invention. However, the present invention is not intended to be limited by these examples.

Example 1

A thermal decomposing process of polystyrene resin was carried out through the following method by using an experimental device as shown in FIG. 2.

To a flask (9) were loaded 80 g of polystyrene resin and 8 g of magnesium sulfate heptahydrate ($MgSO_4 7H_2O$), and this was subjected to a heating process by heating the inside of the flask (9) by a mantle heater (11) while being mixed and stirred by stirring blades (10); and the liquid temperature was measured by a thermometer (14) and the outlet temperature of thermally decomposed vapors was measured by a thermometer (15).

Thermally decomposed vapors generated in the flask are condensed and liquefied by a cooling tube (12) connected to the outlet of the flask(9), and the resulting liquid was collected into a collecting bin (13).

The amount of the liquid collected in the collecting bin (13) was 72.91 g (recovery: 91.14%), and the components of the recovered liquid in the collecting bin (13) were analyzed by gas chromatography; and the results show that the content of styrene monomers is as high as 90.0156%, and the contents of toluene and ethylbenzene, which are low-molecular components, are as low as 2.5394% and 0.8776% respectively. Here, FIG. 3 is a chart showing the results of the gas chromatography analyses, and FIG. 4 shows numeric value data of the results of the gas chromatography analyses.

Here, with respect to temperatures while the liquid had being distilled, the liquid temperature was 240 to 260° C., and the thermally decomposed vapor temperature was 145 to 147° C.

Then, the recovered liquid was vacuum-distilled so that styrene monomer having a purity of 99.92% which satisfies the purity of 99.5% conforming to JIS standard was obtained.

Example 2

A thermal decomposing process of polystyrene resin was carried out through the following method by using an experimental device as shown in FIG. 5.

To a flask (9) were loaded 50 g of polystyrene resin and 9.65 g of magnesium sulfate ($MgSO_4$) calcined at 500° C., and a net plate (16) was placed at an upper position inside the flask (9), and Raschig rings of ø5 mm, made of ceramics, were put onto the net plate (16) so as to form a filled substance layer (17).

This was subjected to a heating process by heating the inside of the flask (9) by a mantle heater (11) while being mixed and stirred by stirring blades (10); and the liquid temperature was measured by a thermometer (14) and the outlet temperature of thermally decomposed vapors was measured by a thermometer (15). Here, a ribbon heater (not shown) was wound around the outlet of the flask (9) so as to apply heat thereto. The heating process by this ribbon heater was made so as to preliminary heat the path from the outlet of the flask to the cooling tube to not less than 145° C.; thus, it became possible to prevent the initially distilled portion of the vapor taken out from the outlet of the flask from being liquefied and again dropping inside the flask before reaching the cooling tube.

Thermally decomposed vapors generated in the flask were condensed and liquefied by a cooling tube (12) connected to the outlet of the flask(9), and the resulting liquid was collected into a collecting bin (13).

The components of the recovered liquid in the collecting bin (13) were analyzed by gas chromatography; and the results show that the content of styrene monomers is as high as 96.1607%, and the contents of toluene and ethylbenzene, which are low-molecular components, are as low as 1.9955% and 0.2363% respectively. Here, FIG. 6 is a chart showing the results of the gas chromatography analyses, and FIG. 7 show numeric value data of the results of the gas chromatography analyses.

Here, with respect to temperatures while the liquid had being distilled, the liquid temperature was 257 to 334° C., and the thermally decomposed vapor temperature was 159.0 to 199.6° C.

Example 3

A thermal decomposing process of polystyrene resin was carried out through the following method by using an experimental device as shown in FIG. 5.

To a flask (9) were loaded 100 g of polystyrene resin and 20 g of magnesium sulfate ($MgSO_4$) calcined at 800° C., and a net plate (16) was placed at an upper position inside the flask (9), and Raschig rings of ø5 mm, made of ceramics, were put onto the net plate (16) so as to form a filled substance layer (17).

This was subjected to a heating process by heating the inside of the flask (9) by a mantle heater (11) while being mixed and stirred by stirring blades (10); and the liquid temperature was measured by a thermometer (14) and the outlet temperature of thermally decomposed vapors was measured by a thermometer (15). Here, a ribbon heater (not shown) was wound around the outlet of the flask (9) so as to apply heat thereto in the same manner as Example 2.

Thermally decomposed vapors generated in the flask were condensed and liquefied by a cooling tube (12) connected to the outlet of the flask(9), and the resulting liquid was collected into a collecting bin (13).

The components of the recovered liquid in the collecting bin (13) were analyzed by gas chromatography; and the results show that the content of styrene monomers is as high as 94.5081%, and the contents of toluene and ethylbenzene, which are low-molecular components, are as low as 2.4536% and 0.3544% respectively. Here, FIG. 8 is a chart showing the results of the gas chromatography analyses, and FIG. 9 shows numeric value data of the results of the gas chromatography analyses.

Here, with respect to temperatures while the liquid had being distilled, the liquid temperature was 306.5 to 324.9° C., and the thermally decomposed vapor temperature was 154.8 to 203.3° C.

Example 4

A thermal decomposing process of polystyrene resin was carried out through the following method by using an experimental device as shown in FIG. 5.

To a flask (9) were loaded 60 g of polystyrene resin and 15 g of sodium sulfate ($Na_2SO_4$), and a net plate (16) was placed at an upper position inside the flask (9), and Raschig rings of ø5 mm, made of ceramics, were put onto the net plate (16) so as to form a filed substance layer (17).

This was subjected to a heating process by heating the inside of the flask (9) by a mantle heater (11) while being mixed and stirred by stirring blades (10); and the liquid temperature was measured by a thermometer (14) and the outlet temperature of thermally decomposed vapors was measured by a thermometer (15). Here, a ribbon heater (not shown) was wound around the outlet of the flask (9) so as to apply heat thereto in the same manner as Example 2.

Thermally decomposed vapors generated in the flask were condensed and liquefied by a cooling tube (12) connected to the outlet of the flask(9), and the resulting liquid was collected into a collecting bin (13).

The components of the recovered liquid in the collecting bin (13) were analyzed by gas chromatography; and the results show that the content of styrene monomers is as high as 89.4618%, and the contents of toluene and ethylbenzene, which are low-molecular components, are as low as 2.2737% and 5.4044% respectively. Here, FIG. 10 is a chart showing the results of the gas chromatography analyses, and FIG. 11 shows numeric value data of the results of the gas chromatography analyses.

Here, with respect to temperatures while the liquid had being distilled, the liquid temperature was 286 to 328° C., and the thermally decomposed vapor temperature was 210 to 234.6° C.

Example 5

A thermal decomposing process of polystyrene resin was carried out through the following method by using an experimental device as shown in FIG. 5.

To a flask (9) were loaded 80 g of polystyrene resin and 20 g of iron sulfate (FeSO$_4$), and a net plate (16) was placed at an upper position inside the flask (9), and Raschig rings of ø5 mm, made of ceramics, were put onto the net plate (16) so as to form a filled substance layer (17).

This was subjected to a heating process by heating the inside of the flask (9) by a mantle heater (11) while being mixed and stirred by stirring blades (10); and the liquid temperature was measured by a thermometer (14) and the outlet temperature of thermally decomposed vapors was measured by a thermometer (15). Here, a ribbon heater (not shown) was wound around the outlet of the flask (9) so as to apply heat thereto in the same manner as Example 2.

Thermally decomposed vapors generated in the flask were condensed and liquefied by a cooling tube (12) connected to the outlet of the flask(9), and the resulting liquid was collected into a collecting bin (13).

The components of the recovered liquid in the collecting bin (13) were analyzed by gas chromatography; and the results show that the content of styrene monomers is as high as 92.9584%, and the contents of toluene and ethylbenzene, which are low-molecular components, are as low as 2.5875% and 0.7139% respectively. Here, FIG. 12 is a chart showing the results of the gas chromatography analyses, and FIG. 13 shows numeric value data of the results of the gas chromatography analyses.

Here, with respect to temperatures while the liquid had being distilled, the liquid temperature was 192.0 to 306.5° C., and the thermally decomposed vapor temperature was 157.7 to 261.4° C.

Example 6

A thermal decomposing process of polystyrene resin was carried out through the following method by using an experimental device as shown in FIG. 5.

To a flask (9) were loaded 100 g of polystyrene resin and 20 g of manganese sulfate (MnSO$_4$), and a net plate (16) was placed at an upper position inside the flask (9), and Raschig rings of ø5 mm, made of ceramics, were put onto the net plate (16) so as to form a filled substance layer (17).

This was subjected to a heating process by heating the inside of the flask (9) by a mantle heater (11) while being mixed and stirred by stirring blades (10); and the liquid temperature was measured by a thermometer (14) and the outlet temperature of thermally decomposed vapors was measured by a thermometer (15). Here, a ribbon heater (not shown) was wound around the outlet of the flask (9) so as to apply heat thereto in the same manner as Example 2.

Thermally decomposed vapors generated in the flask were condensed and liquefied by a cooling tube (12) connected to the outlet of the flask(9), and the resulting liquid was collected into a collecting bin (13).

The components of the recovered liquid in the collecting bin (13) were analyzed by gas chromatography; and the results show that the content of styrene monomers is as high as 96.6863%, and the contents of toluene and ethylbenzene, which are low-molecular components, are as low as 1.8501% and 0.3731% respectively. Here, FIG. 14 is a chart showing the results of the gas chromatography analyses, and FIG. 15 shows numeric value data of the results of the gas chromatography analyses.

Here, with respect to temperatures while the liquid had being distilled, the liquid temperature was 200.8 to 340.2° C., and the thermally decomposed vapor temperature was 145.4 to 180.4° C.

Example 7

A thermal decomposing process of polystyrene resin was carried out through the following method by using an experimental device as shown in FIG. 5.

To a flask (9) were loaded 100 g of polystyrene resin and 20 g of zinc sulfate (ZnSO$_4$), and a net plate (16) was placed at an upper position inside the flask (9), and Raschig rings of ø5 mm, made of ceramics, were put onto the net plate (16) so as to form a filled substance layer (17).

This was subjected to a heating process by heating the inside of the flask (9) by a mantle heater (11) while being mixed and stirred by stirring blades (10); and the liquid temperature was measured by a thermometer (14) and the outlet temperature of thermally decomposed vapors was measured by a thermometer (15). Here, a ribbon heater (not shown) was wound around the outlet of the flask (9) so as to apply heat thereto in the same manner as Example 2.

Thermally decomposed vapors generated in the flask were condensed and liquefied by a cooling tube (12) connected to the outlet of the flask(9), and the resulting liquid was collected into a collecting bin (13).

The components of the recovered liquid in the collecting bin (13) were analyzed by gas chromatography; and the results show that the content of styrene monomers is as high as 92.1085%, and the contents of toluene and ethylbenzene, which are low-molecular components, are as low as 3.3474% and 0.8941% respectively. Here, FIG. 16 is a chart showing the results of the gas chromatography analyses, and FIG. 17 shows numeric value data of the results of the gas chromatography analyses.

Here, with respect to temperatures while the liquid had being distilled, the liquid temperature was 196.0 to 351.2° C., and the thermally decomposed vapor temperature was 146.3 to 241.3° C.

Example 8

A thermal decomposing process of polystyrene resin was carried out through the following method by using an experimental device as shown in FIG. 5.

To a flask (9) were loaded 100 g of polystyrene resin and 20 g of aluminum sulfate ($Al_2(SO_4)_3$), and a net plate (16) was placed at an upper position inside the flask (9), and Raschig rings of ø5 mm, made of ceramics, were put onto the net plate (16) so as to form a filled substance layer (17).

This was subjected to a heating process by heating the inside of the flask (9) by a mantle heater (11) while being mixed and stirred by stirring blades (10); and the liquid temperature was measured by a thermometer (14) and the outlet temperature of thermally decomposed vapors was measured by a thermometer (15). Here, a ribbon heater (not shown) was wound around the outlet of the flask (9) so as to apply heat thereto in the same manner as Example 2.

Thermally decomposed vapors generated in the flask were condensed and liquefied by a cooling tube (12) connected to the outlet of the flask(9), and the resulting liquid was collected into a collecting bin (13).

The components of the recovered liquid in the collecting bin (13) were analyzed by gas chromatography; and the results show that the content of styrene monomers is as high as 95.0094%, and the contents of toluene and ethylbenzene, which are low-molecular components, are as low as 2.0112% and 0.9381% respectively. Here, FIG. 18 is a chart showing the results of the gas chromatography analyses, and FIG. 19 shows numeric value data of the results of the gas chromatography analyses.

Here, with respect to temperatures while the liquid had being distilled, the liquid temperature was 202.3 to 304.3° C., and the thermally decomposed vapor temperature was 145.7 to 172.4° C.

Example 9

A thermal decomposing process of polystyrene resin was carried out through the following method by using an experimental device as shown in FIG. 5.

To a flask (9) were loaded 100 g of polystyrene resin and 20 g of calcium sulfate ($CaSO_4$), and a net plate (16) was placed at an upper position inside the flask (9), and Raschig rings of ø5 mm, made of ceramics, were put onto the net plate (16) so as to form a filled substance layer (17).

This was subjected to a heating process by heating the inside of the flask (9) by a mantle heater (11) while being mixed and stirred by stirring blades (10); and the liquid temperature was measured by a thermometer (14) and the outlet temperature of thermally decomposed vapors was measured by a thermometer (15). Here, a ribbon heater (not shown) was wound around the outlet of the flask (9) so as to apply heat thereto in the same manner as Example 2.

Thermally decomposed vapors generated in the flask were condensed and liquefied by a cooling tube (12) connected to the outlet of the flask(9), and the resulting liquid was collected into a collecting bin (13).

The components of the recovered liquid in the collecting bin (13) were analyzed by gas chromatography; and the results show that the content of styrene monomers is as high as 94.3744%, and the contents of toluene and ethylbenzene, which are low-molecular components, are as low as 2.7867% and 0.4139% respectively. Here, FIG. 20 is a chart showing the results of the gas chromatography analyses, and FIG. 21 shows numeric value data of the results of the gas chromatography analyses.

Here, with respect to temperatures while the liquid had being distilled, the liquid temperature was 211.6 to 303.8° C., and the thermally decomposed vapor temperature was 146.3 to 197.5° C.

Example 10

A thermal decomposing process of polystyrene resin was carried out through the following method by using an experimental device as shown in. FIG. 5.

To a flask (9) were loaded 100 g of polystyrene resin and 20 g of potassium sulfate ($K_2SO_4$), and a net plate (16) was placed at an upper position inside the flask (9), and Raschig rings of ø5 mm, made of ceramics, were put onto the net plate (16) so as to form a filled substance layer (17).

This was subjected to a heating process by heating the inside of the flask (9) by a mantle heater (11) while being mixed and stirred by stirring blades (10); and the liquid temperature was measured by a thermometer (14) and the outlet temperature of thermally decomposed vapors was measured by a thermometer (15). Here, a ribbon heater (not shown) was wound around the outlet of the flask (9) so as to apply heat thereto in the same manner as Example 2.

Thermally decomposed vapors generated in the flask were condensed and liquefied by a cooling tube (12) connected to the outlet of the flask(9), and the resulting liquid was collected into a collecting bin (13).

The components of the recovered liquid in the collecting bin (13) were analyzed by gas chromatography; and the results show that the content of styrene monomers is as high as 90.4612%, and the contents of toluene and ethylbenzene, which are low-molecular components, are as low as 2.5724% and 1.3448% respectively. Here, FIG. 22 is a chart showing the results of the gas chromatography analyses, and FIG. 23 shows numeric value data of the results of the gas chromatography analyses.

Here, with respect to temperatures while the liquid had being distilled, the liquid temperature was 301.3 to 350.6° C., and the thermally decomposed vapor temperature was 148.6 to 178.7° C.

Example 11

A thermal decomposing process of polystyrene resin was carried out through the following method by using an experimental device as shown in FIG. 5.

To a flask (9) were loaded 50 g of polystyrene resin and 10 g of antimony sulfate ($Sb_2(SO_4)_3$), and a net plate (16) was placed at an upper position inside the flask (9), and Raschig rings of ø5 mm, made of ceramics, were put onto the net plate (16) so as to form a filled substance layer (17).

This was subjected to a heating process by heating the inside of the flask (9) by a mantle heater (11) while being mixed and stirred by stirring blades (10); and the liquid temperature was measured by a thermometer (14) and the outlet temperature of thermally decomposed vapors was measured by a thermometer (15). Here, a ribbon heater (not shown) was wound around the outlet of the flask (9) so as to apply heat thereto in the same manner as Example 2.

Thermally decomposed vapors generated in the flask were condensed and liquefied by a cooling tube (12) connected to the outlet of the flask(9), and the resulting liquid was collected into a collecting bin (13).

The components of the recovered liquid in the collecting bin (13) were analyzed by gas chromatography; and the results show that the content of styrene monomers is as high as 90.8510%, and the contents of toluene and ethylbenzene, which are low-molecular components, are as low as 2.1073% and 0.2313% respectively. Here, FIG. 24 shows numeric value data of the results of the gas chromatography analyses.

Here, with respect to temperatures while the liquid had being distilled, the liquid temperature was 250.6 to 301.3°

C., and the thermally decomposed vapor temperature was 149.1 to 185.8° C.

As described above, the method for recovering styrene monomers from polystyrene resins by using a catalyst of the present invention makes it possible to recover oil containing less ratio of low molecular weight components such as toluene and ethylbenzene and a high content of styrene monomers from vapors obtained through thermal decomposition of polystyrene resins.

Moreover, the present method makes it possible to thermally decompose polystyrene resins at comparatively low temperatures for a short time, and to reduce catalyst costs; thus, it is possible to provide styrene monomers with high production efficiency.

BRIEF DESCRIPTION OF THE DRAWINGS

FIG. 4 shows numeric data of the results of gas chromatography analyses on distilled products (crude styrene monomers) obtained in Example 2.

FIG. 7 shows numeric value data of the results of gas chromatography analyses on distilled products (crude styrene monomers) obtained in Example 2.

FIG. 9 shows numeric value data of the results of gas chromatography analyses on distilled products (crude styrene monomers) obtained in Example 3.

FIG. 11 shows numeric value data of the results of gas chromatography analyses on distilled products (crude styrene monomers) obtained in Example 4.

FIG. 13 shows numeric value data of the results of gas chromatography analyses on distilled products (crude styrene monomers) obtained in Example 5.

FIG. 15 shows numeric value data of the results of gas chromatography analyses on distilled products (crude styrene monomers) obtained in Example 6.

FIG. 17 shows numeric value data of the results of gas chromatography analyses on distilled products (crude styrene monomers) obtained in Example 7.

FIG. 19 shows numeric value data of the results of gas chromatography analyses on distilled products (crude styrene monomers) obtained in Example 8.

FIG. 21 shows numeric value data of the results of gas chromatography analyses on distilled products (crude styrene monomers) obtained in Example 9.

FIG. 23 shows numeric value data of the results of gas chromatography analyses on distilled products (crude styrene monomers) obtained in Example 10.

FIG. 24 is a chart that shows the results of gas chromatography analyses on distilled products (crude styrene monomers) obtained in Example 11.

Figure 1:
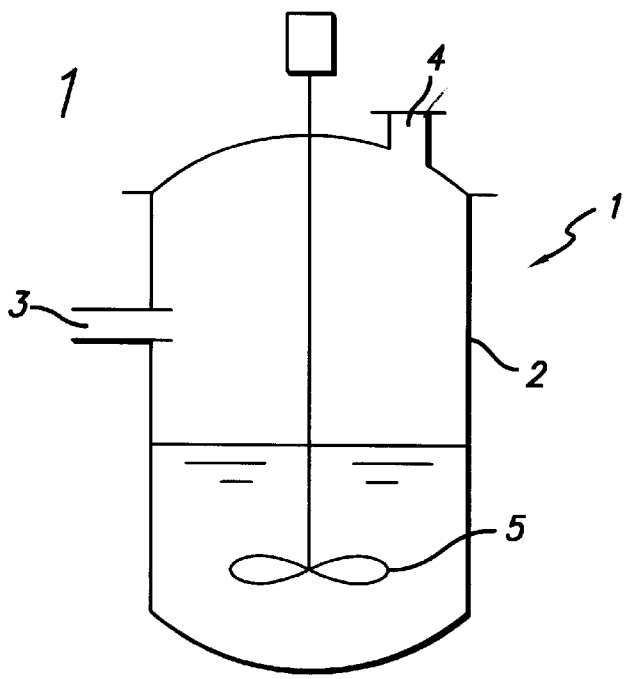
FIG. 1 is a schematic view showing one example of a thermal decomposing device used in the present invention.
Figure 2:
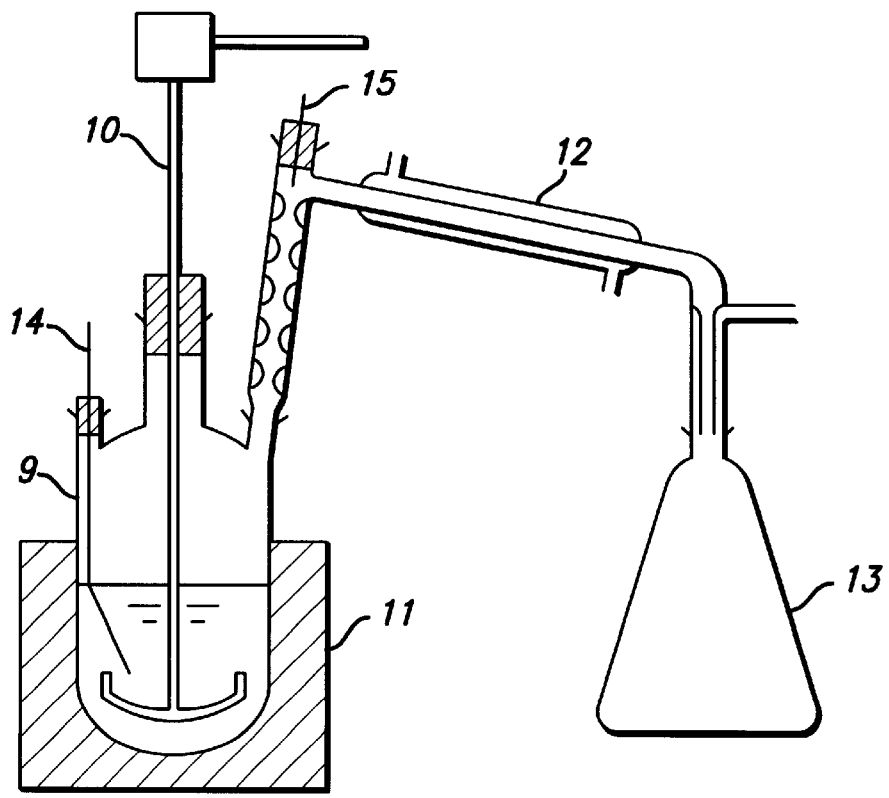
FIG. 2 is a schematic view showing one example of an experimental device used in Example 1 of the present invention.
Figure 3:
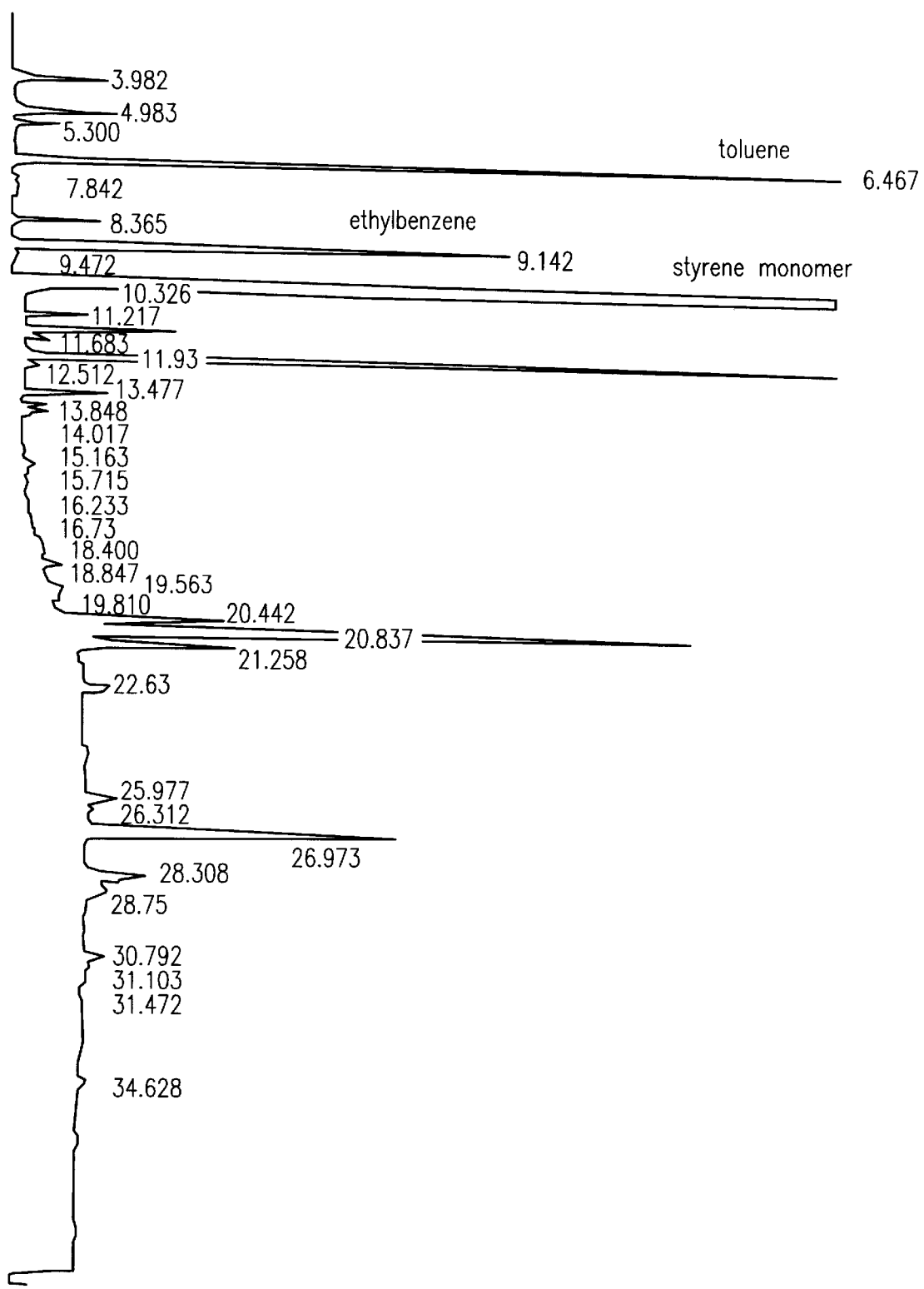
FIG. 3 is a chart that shows the results of gas chromatography analyses on distilled products (crude styrene monomers) obtained in Example 1.
Figure 5:
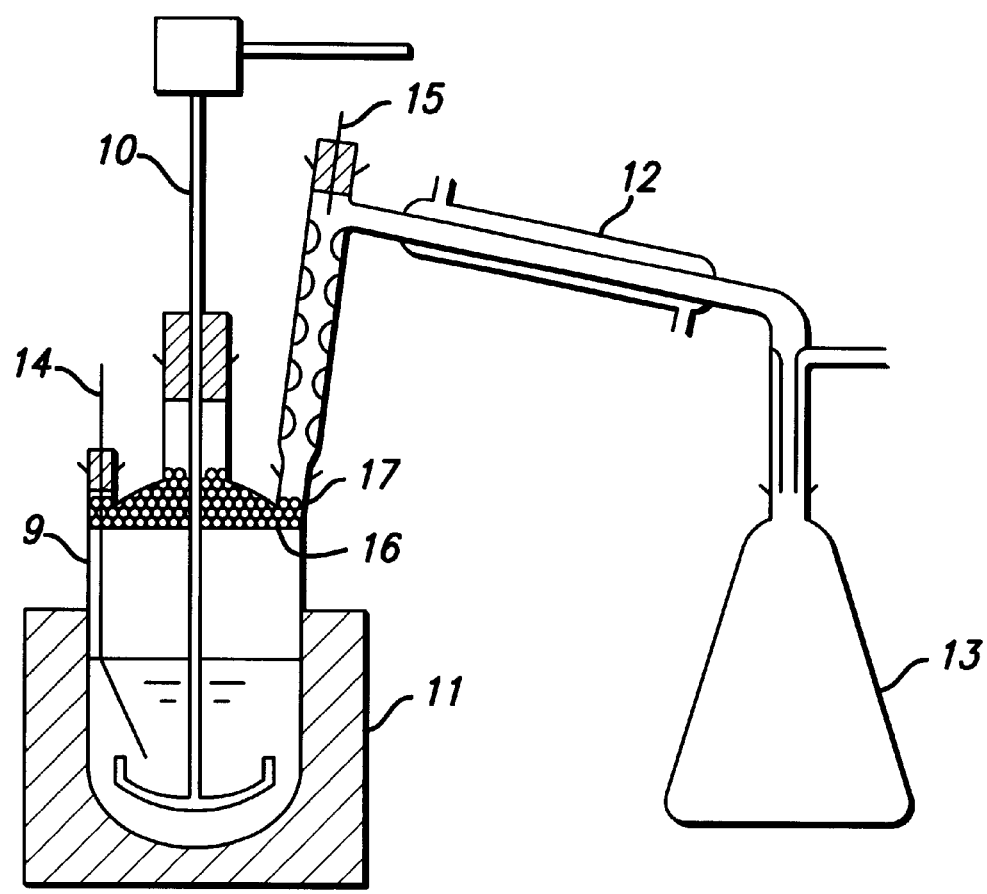
FIG. 5 is a schematic view showing one example of an experimental device used in Examples 2 through 11 of the present invention.
Figure 6:
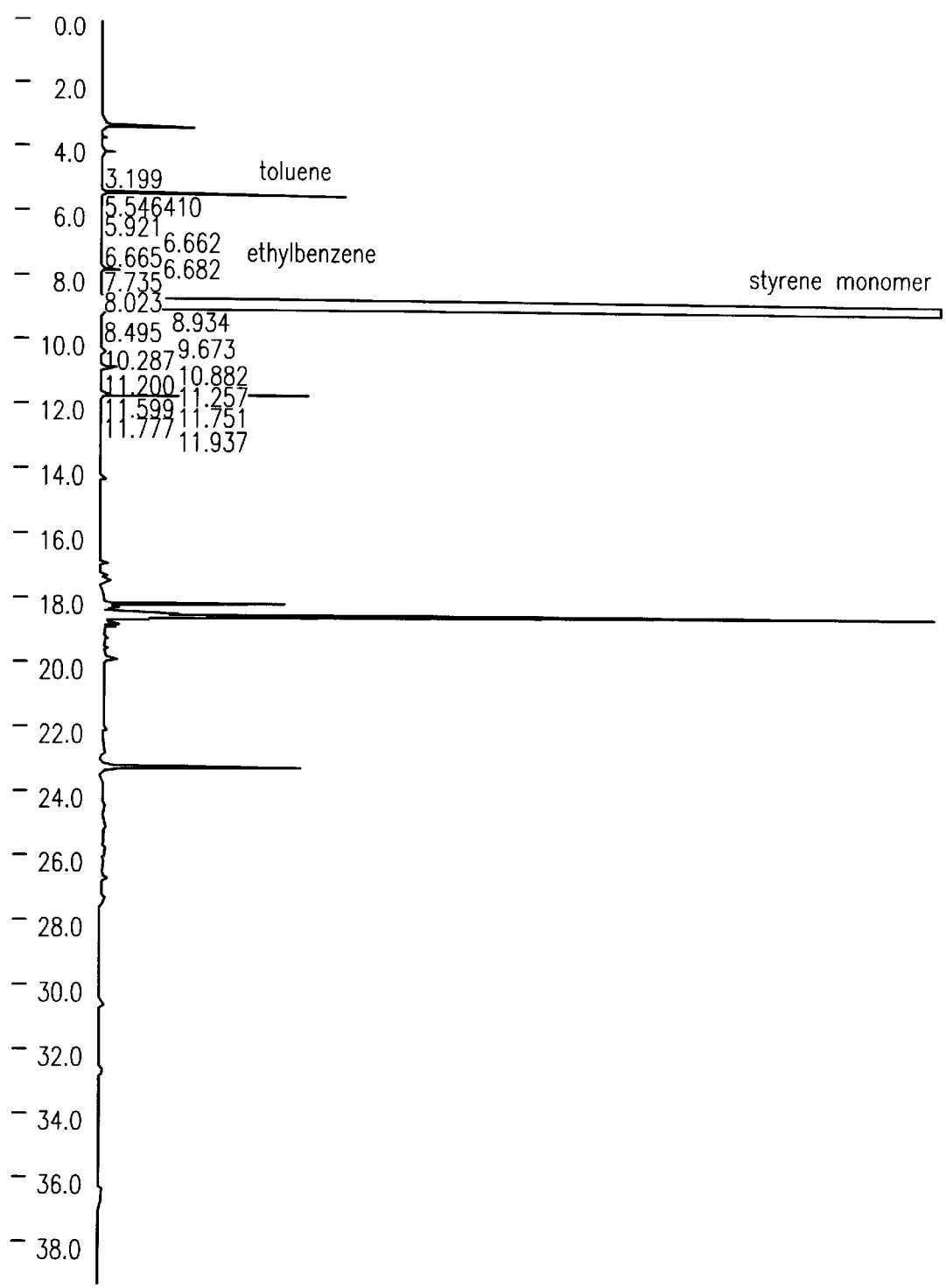
FIG. 6 is a chart that shows the results of gas chromatography analyses on distilled products (crude styrene monomers) obtained in Example 2.
Figure 8:
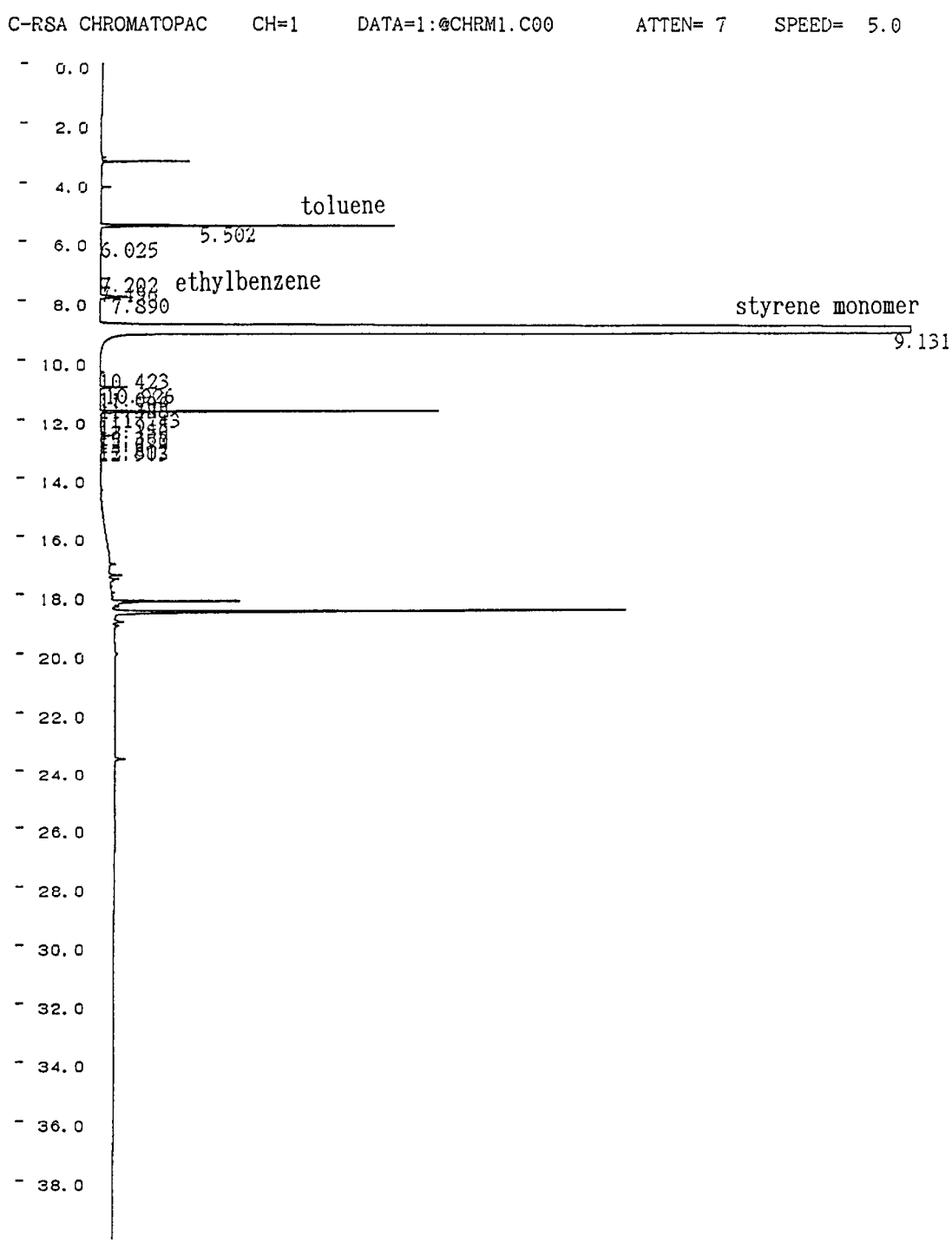
FIG. 8 is a chart that shows the results of gas chromatography analyses on distilled products (crude styrene monomers) obtained in Example 3.
Figure 10:
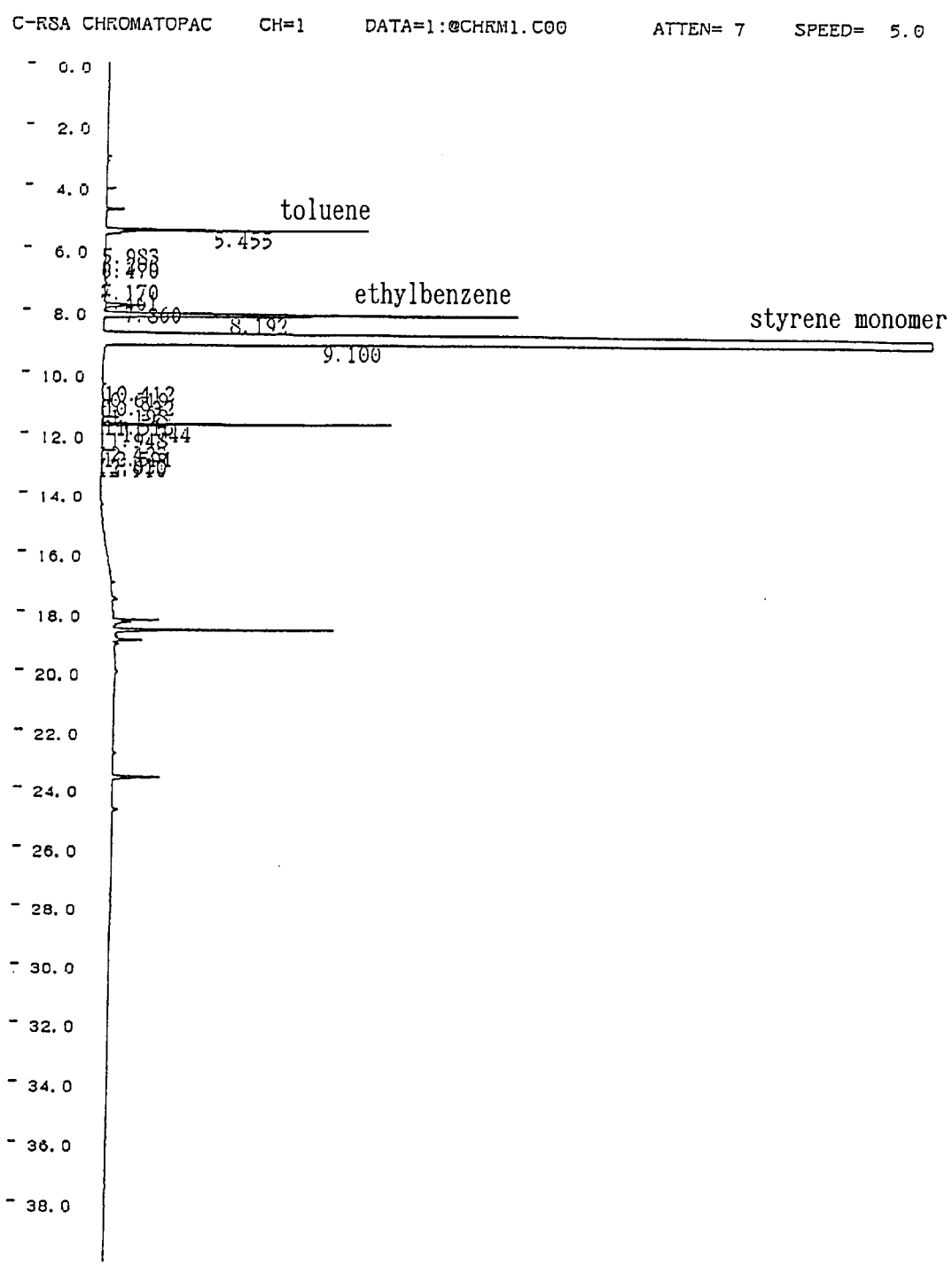
FIG. 10 is a chart that shows the results of gas chromatography analyses on distilled products (crude styrene monomers) obtained in Example 4.
Figure 12:
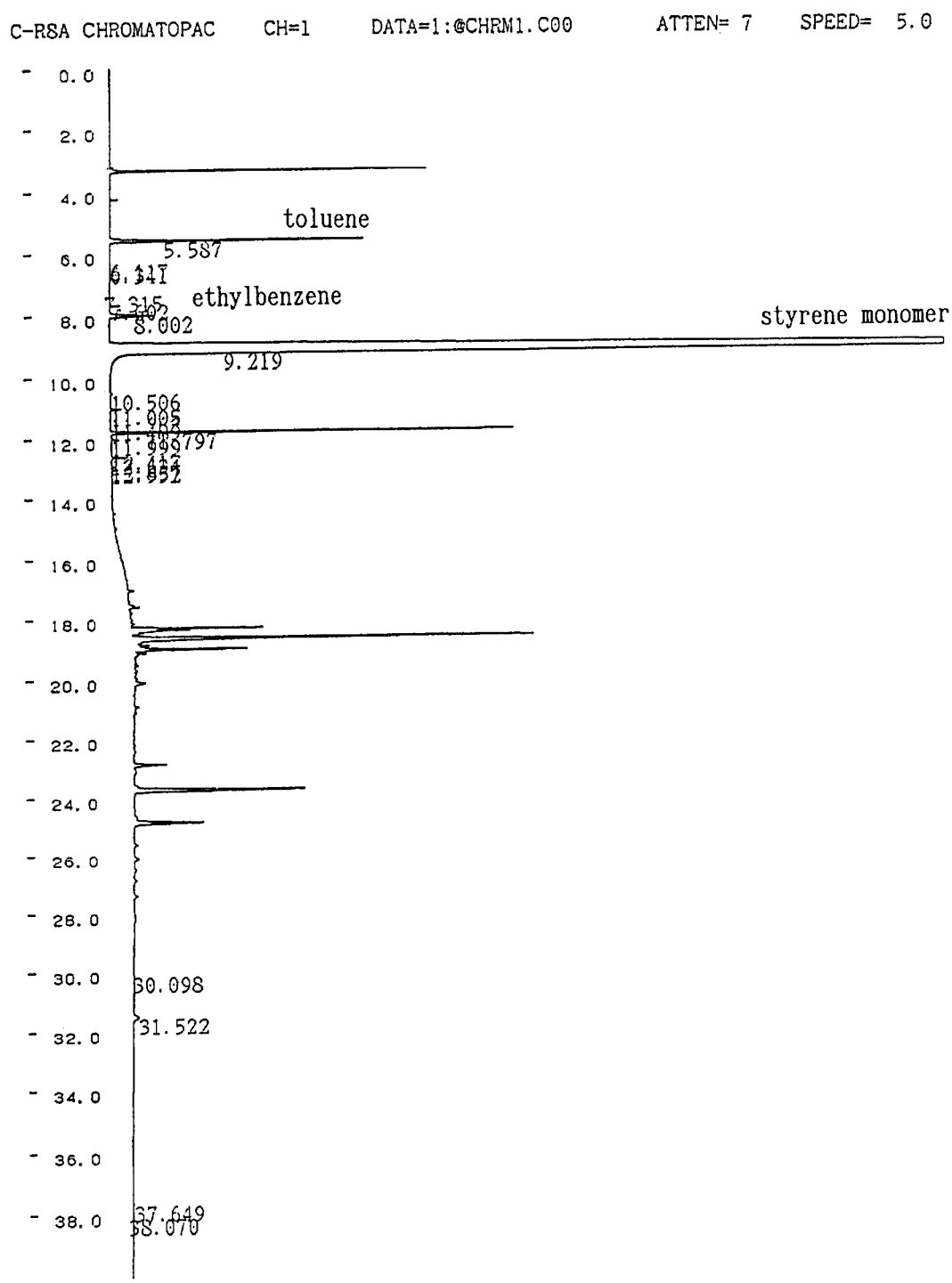
FIG. 12 is a chart that shows the results of gas chromatography analyses on distilled products (crude styrene monomers) obtained in Example 5.
Figure 14:
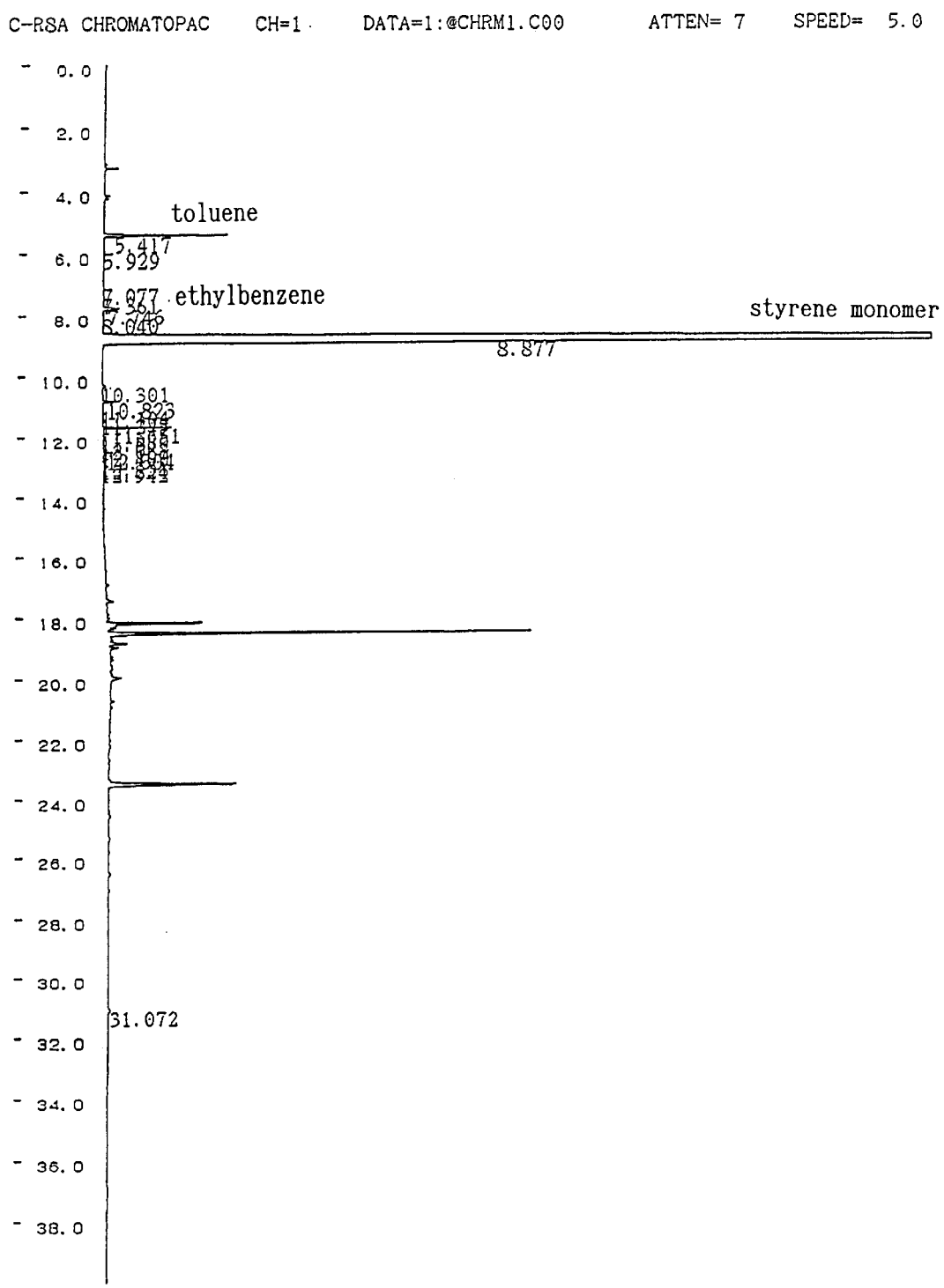
FIG. 14 is a chart that shows the results of gas chromatography analyses on distilled products (crude styrene monomers) obtained in Example 6.
Figure 16:
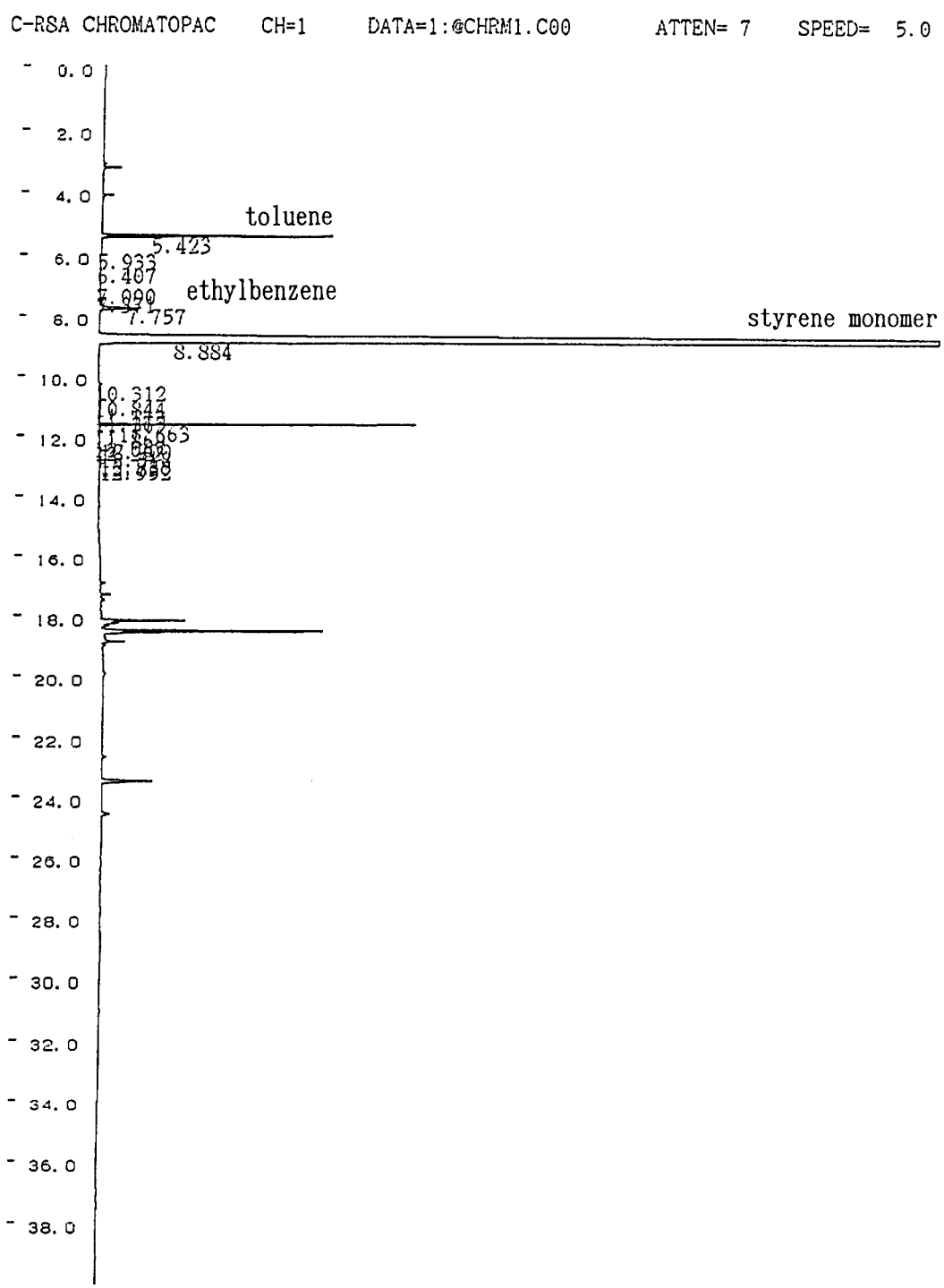
FIG. 16 is a chart that shows the results of gas chromatography analyses on distilled products (crude styrene monomers) obtained in Example 7.
Figure 18:
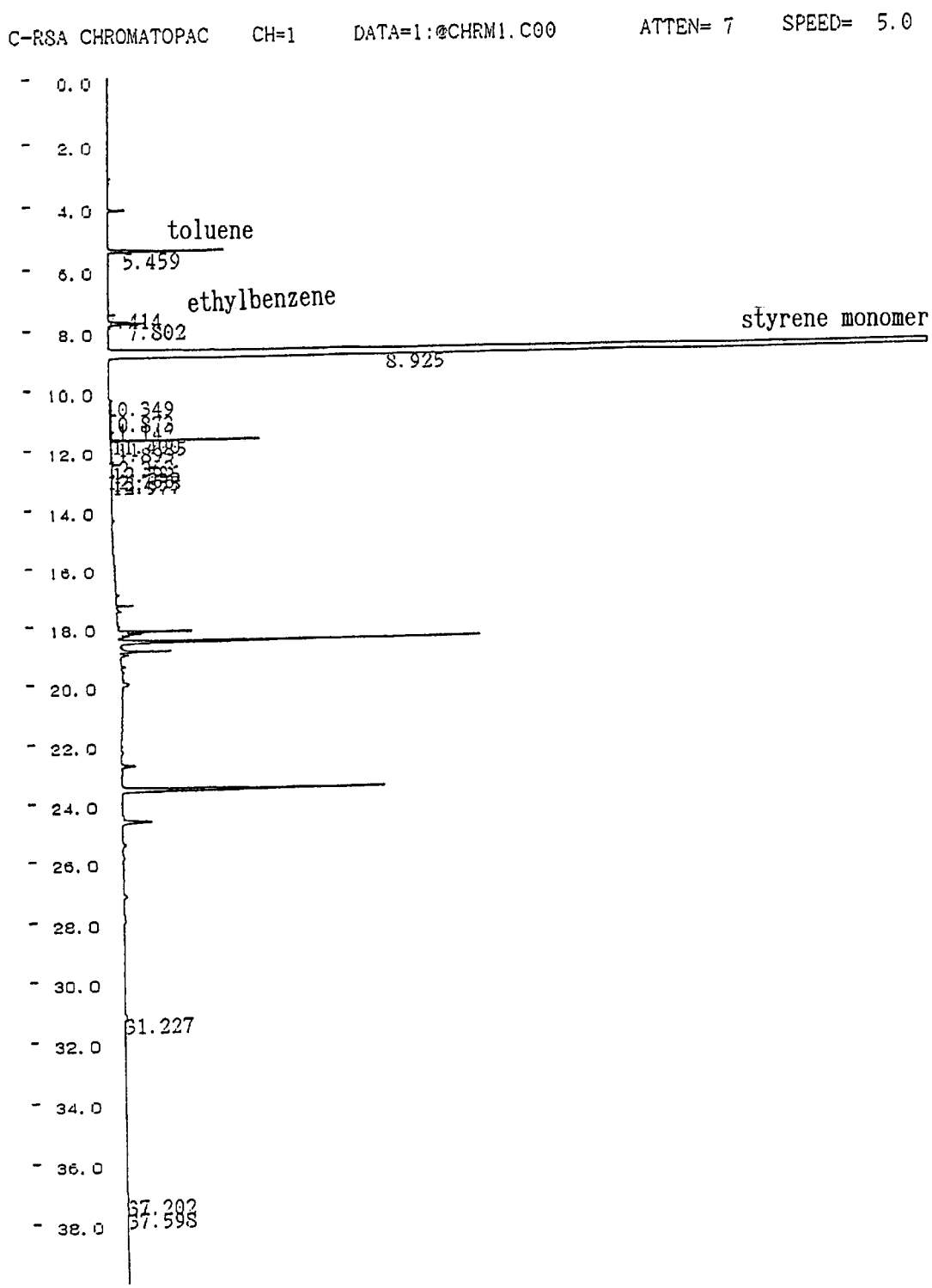
FIG. 18 is a chart that shows the results of gas chromatography analyses on distilled products (crude styrene monomers) obtained in Example 8.
Figure 20:
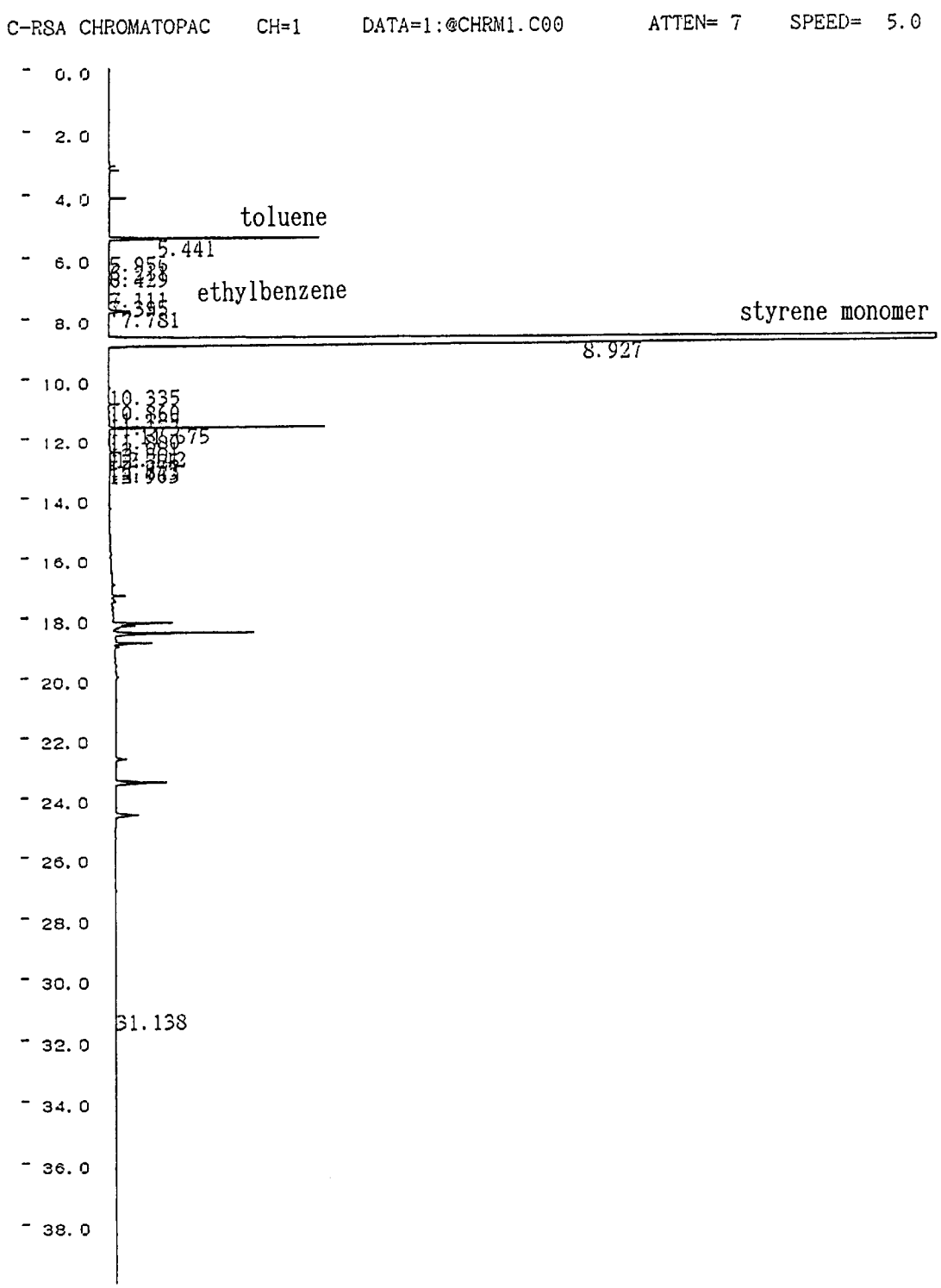
FIG. 20 is a chart that shows the results of gas chromatography analyses on distilled products (crude styrene monomers) obtained in Example 9.
Figure 22:
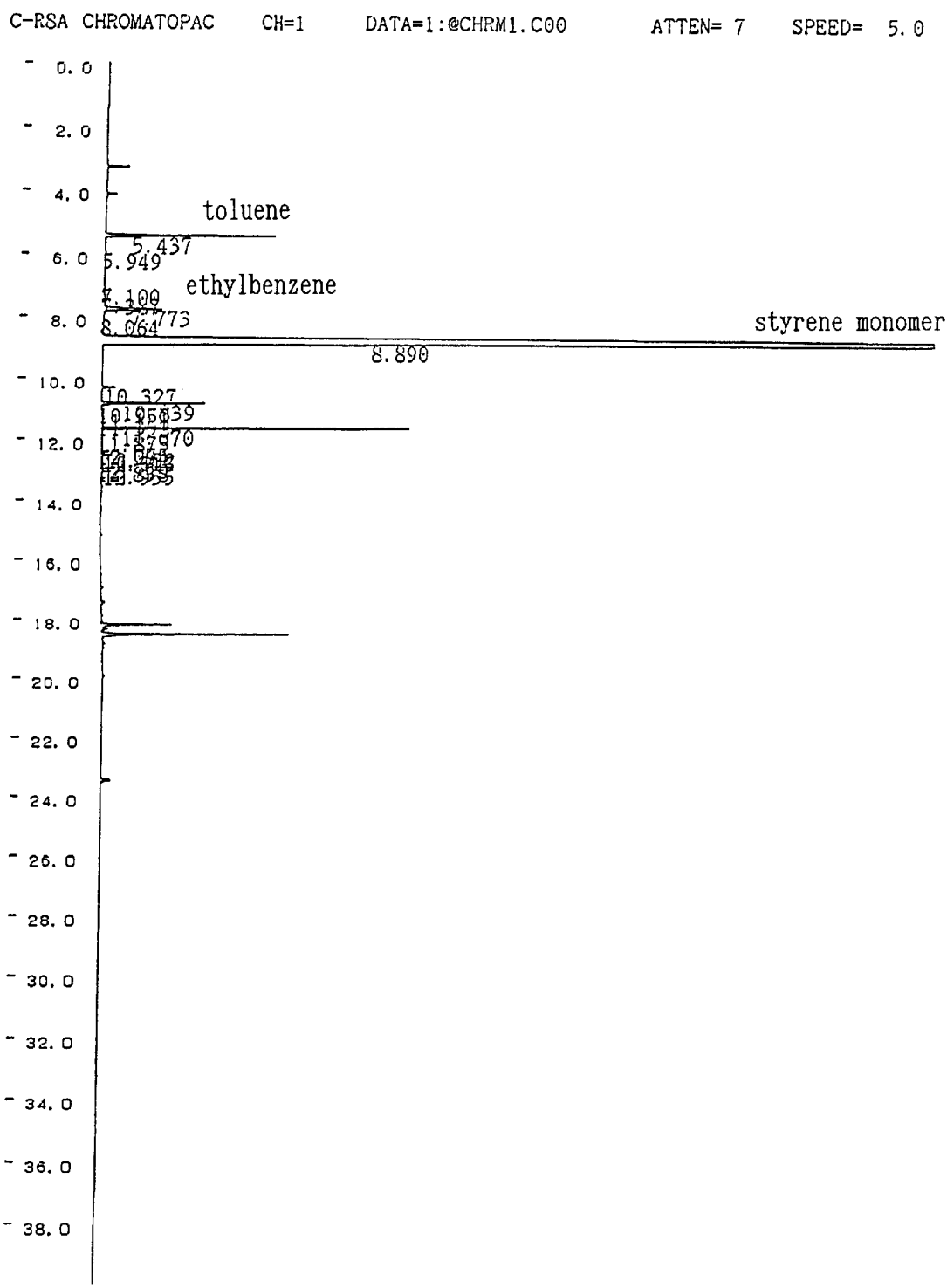
FIG. 22 is a chart that shows the results of gas chromatography analyses on distilled products (crude styrene monomers) obtained in Example 10.

What is claimed is:

1. A method for recovering styrene monomers from polystyrene resin by a step of depolymerizing the polystyrene resin with heating to produce said styrene monomers in the presence of a catalyst which is selected from the group consisting of magnesium sulfate, sodium sulfate, iron sulfate, aluminum sulfate, calcium sulfate, potassium sulfate, antimony sulfate, and the mixture of two or more thereof.

2. The method for recovering styrene monomers from the polystyrene resin gained by catalyst method according to claim 1, wherein the heating temperature of the polystyrene resin is 350° C. or less.

3. A method for recovering styrene monomers from a polystyrene resin by using a catalyst, which obtains the styrene monomers by thermally decomposing the polystyrene resin, comprising the steps:

providing a polystyrene resin;

adding a sulfate compound to said polystyrene resin, said sulfate compound acting as a catalyst which is selected from the group consisting of magnesium sulfate, sodium sulfate, iron sulfate, aluminum sulfate, calcium sulfate, potassium sulfate, antimony sulfate, and the mixture of two or more thereof; and providing heat at a heating temperature, said heat thermally decomposing said styrene resin in the presence of only said sulfate catalyst, said sulfate catalyst promoting decomposition of said styrene resin to styrene monomer; whereby polystyrene resin is converted to styrene monomer in a safer and less toxic manner.

4. The method for recovering styrene monomers from a polystyrene resin by using a catalyst according to claim 3, further comprising:

wherein said heating temperature of the polystyrene resin is not more than 350° C.

* * * * *